United States Patent
Li et al.

(10) Patent No.: US 8,069,020 B2
(45) Date of Patent: *Nov. 29, 2011

(54) GENERATING SIMULATED DIFFRACTION SIGNAL USING A DISPERSION FUNCTION RELATING PROCESS PARAMETER TO DISPERSION

(75) Inventors: Shifang Li, Pleasanton, CA (US); Hanyou Chu, Palo Alto, CA (US)

(73) Assignee: Tokyo Electron Limited, Tokyo (JP)

( * ) Notice: Subject to any disclaimer, the term of this patent is extended or adjusted under 35 U.S.C. 154(b) by 714 days.

This patent is subject to a terminal disclaimer.

(21) Appl. No.: 11/858,058

(22) Filed: Sep. 19, 2007

(65) Prior Publication Data

US 2009/0076782 A1    Mar. 19, 2009

(51) Int. Cl.
G06G 7/48 (2006.01)
(52) U.S. Cl. ........... 703/6; 703/1; 703/2; 703/13; 702/1; 702/40; 702/127; 702/159; 702/189; 438/14; 438/16; 356/300; 356/306
(58) Field of Classification Search .............. 438/14, 438/16; 703/6, 1, 2, 13; 706/12, 14, 46; 356/300, 337, 639, 306; 716/4; 702/1, 40, 702/127, 159, 189

See application file for complete search history.

(56) References Cited

U.S. PATENT DOCUMENTS

| | | | | |
|---|---|---|---|---|
| 5,796,483 A * | 8/1998 | Nakayama | ................ | 356/490 |
| 6,192,103 B1 * | 2/2001 | Wormington et al. | ......... | 378/73 |
| 6,304,999 B1 * | 10/2001 | Toprac et al. | ................ | 716/4 |
| 6,383,888 B1 * | 5/2002 | Stirton | ................ | 438/401 |
| 6,650,422 B2 * | 11/2003 | Singh et al. | ................ | 356/601 |
| 6,728,937 B2 * | 4/2004 | Wakita et al. | ................ | 716/136 |
| 6,791,679 B2 * | 9/2004 | Engelhard et al. | ............ | 356/124 |
| 6,891,626 B2 | 5/2005 | Niu et al. | | |
| 6,895,295 B1 * | 5/2005 | Grover et al. | ................ | 700/121 |
| 6,943,900 B2 * | 9/2005 | Niu et al. | ................ | 356/625 |
| 7,019,850 B2 * | 3/2006 | Finarov | ................ | 356/630 |
| 7,054,561 B2 * | 5/2006 | Fabiny | ................ | 398/82 |
| 7,072,049 B2 * | 7/2006 | Niu et al. | ................ | 356/601 |
| 7,110,886 B2 * | 9/2006 | Ito et al. | ................ | 702/22 |
| 7,171,284 B2 * | 1/2007 | Vuong et al. | ................ | 700/121 |
| 7,274,472 B2 * | 9/2007 | Bischoff | ................ | 356/635 |

(Continued)

OTHER PUBLICATIONS

Bevington, et al., "Data Reduction and Error Analysis for the Physical Sciences", Third Edition, p. 116-177, 2002.

*Primary Examiner* — Kamini S Shah
*Assistant Examiner* — Kibrom Gebresilassie
(74) *Attorney, Agent, or Firm* — Manuel Madriaga (57) ABSTRACT

A first wafer is fabricated using a first value for a process parameter specifying a process condition in fabricating the structure. A first value of a dispersion is measured from the first wafer. A second wafer is fabricated using a second value for the process parameter. A second value of the dispersion is measured from the second wafer. A third wafer is fabricated using a third value for the process parameter. The first, second, and third values for the process parameter are different from each other. A third value of the dispersion is measured from the third wafer. A dispersion function is defined to relate the process parameter to the dispersion using the first, second, and third values for the process parameter and the measured first, second, and third values of the dispersion. The simulated diffraction signal is generated using the defined dispersion function. The simulated diffraction signal is stored.

14 Claims, 8 Drawing Sheets

U.S. PATENT DOCUMENTS

| | | | |
|---|---|---|---|
| 7,330,279 B2* | 2/2008 | Vuong et al. | 356/625 |
| 7,352,453 B2* | 4/2008 | Mieher et al. | 356/125 |
| 7,372,583 B1* | 5/2008 | Jin et al. | 356/625 |
| 7,427,521 B2* | 9/2008 | Bischoff et al. | 438/16 |
| 7,515,279 B2* | 4/2009 | Raymond | 356/601 |
| 7,523,076 B2* | 4/2009 | Drege et al. | 706/12 |
| 7,567,352 B2* | 7/2009 | Jin et al. | 356/625 |
| 7,619,731 B2* | 11/2009 | Lally et al. | 356/237.5 |
| 7,636,649 B2* | 12/2009 | Li et al. | 702/188 |
| 7,639,371 B2* | 12/2009 | Raymond | 356/601 |
| 7,912,679 B2* | 3/2011 | Li et al. | 702/189 |
| 2001/0007143 A1* | 7/2001 | Wakita et al. | 716/4 |
| 2002/0131040 A1* | 9/2002 | Niu et al. | 356/237.5 |
| 2002/0165636 A1* | 11/2002 | Hasan | 700/121 |
| 2002/0182760 A1* | 12/2002 | Wack et al. | 438/14 |
| 2003/0152126 A1* | 8/2003 | Okunuki | 372/96 |
| 2003/0223087 A1* | 12/2003 | Sasazawa et al. | 356/636 |
| 2004/0078173 A1* | 4/2004 | Bischoff et al. | 703/2 |
| 2004/0207844 A1* | 10/2004 | Nabatova-Gabain et al. | 356/369 |
| 2004/0265477 A1* | 12/2004 | Nabatova-Gabain et al. | 427/10 |
| 2005/0192914 A1* | 9/2005 | Drege et al. | 706/12 |
| 2006/0187466 A1* | 8/2006 | Li et al. | 356/601 |
| 2006/0262326 A1* | 11/2006 | Abdulhalim et al. | 356/625 |
| 2007/0211260 A1* | 9/2007 | Vuong et al. | 356/625 |
| 2008/0009081 A1* | 1/2008 | Madriaga et al. | 438/16 |
| 2008/0065339 A1* | 3/2008 | Finarov et al. | 702/81 |
| 2008/0087638 A1* | 4/2008 | Brcka et al. | 216/58 |
| 2009/0082993 A1* | 3/2009 | Li et al. | 702/155 |
| 2009/0083013 A1* | 3/2009 | Li et al. | 703/6 |

* cited by examiner

GENERATING SIMULATED DIFFRACTION SIGNAL USING A DISPERSION FUNCTION RELATING PROCESS PARAMETER TO DISPERSION

BACKGROUND

1. Field

The present application generally relates to optical metrology of a structure formed on a semiconductor wafer, and, more particularly, to generating a simulated diffraction signal using a dispersion function relating process parameter to dispersion.

2. Related Art

Optical metrology involves directing an incident beam at a structure, measuring the resulting diffracted beam, and analyzing the diffracted beam to determine one or more profile parameters of the structure. In semiconductor manufacturing, optical metrology is typically used for quality assurance. For example, after the fabrication of a structure on a semiconductor wafer, an optical metrology tool is used to determine the profile of the structure. By determination of the profile of the structure, the quality of the fabrication process utilized to form the structure can be evaluated.

In one conventional optical metrology process, a measured diffraction signal is compared to simulated diffraction signals. The simulated diffraction signals are generated using an optical metrology model. The optical metrology model includes a number of parameters that are varied in generating the simulated diffraction signals. Increasing the number of parameters of the optical metrology model can increase the accuracy of the optical metrology process when those parameters are not correlated to each other. However, parameters are typically correlated to each other to some degree. Thus, increasing the number of parameters of the optical metrology model that are varied can also increase the instability of the model.

DETAILED DESCRIPTION OF EXEMPLARY EMBODIMENT(S)

In order to provide a more thorough understanding of the present invention, the following description sets forth numerous specific details, such as specific configurations, parameters, examples, and the like. It should be recognized, however, that such description is not intended as a limitation on the scope of the present invention, but is intended to provide a better understanding of the exemplary embodiments.

In order to facilitate description of the present invention, a semiconductor wafer may be utilized to illustrate an application of the concept. The methods and processes equally apply to other work pieces that have a structure.

Figure 1:
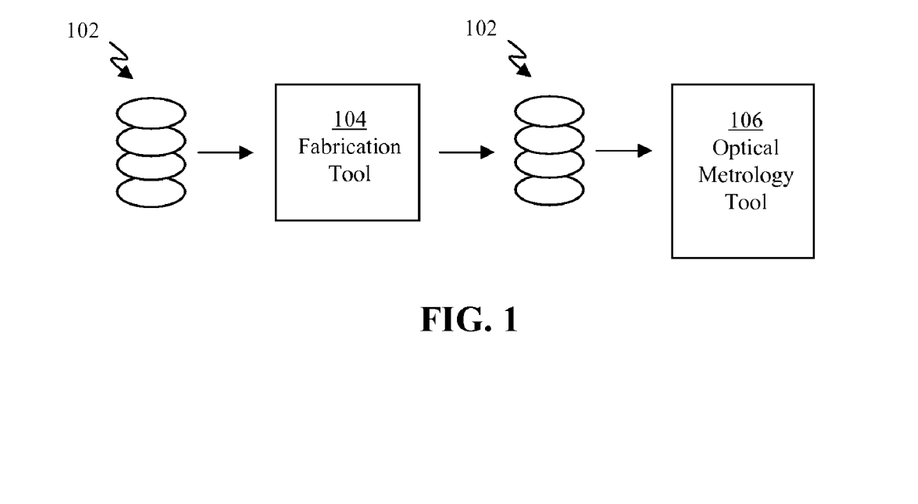
FIG. 1 is an architectural diagram illustrating an exemplary fabrication tool and an exemplary optical metrology tool.

FIG. 1 depicts one or more wafers 102 processed in an exemplary fabrication tool 104. One or more semiconductor fabrication processes can be performed on one or more wafers 102 in fabrication tool 104. Typically a number of wafers 102 are processed as a batch, commonly referred to as a wafer lot, in fabrication tool 104. For example, a wafer lot of 25 wafers 102 can be processed as a batch in fabrication tool 104. It should be recognized, however, that the number of wafers 102 in a wafer lot can vary.

One or more process parameters are used in performing the one or more semiconductor fabrication processes. For example, the one or more process parameters can include deposition conditions, annealing conditions, etching conditions, temperature, gas pressure, vaporization speed, and the like. The etching conditions can include surface property changes, etching residual components, and the like.

Typically, the one or more process parameters are set to define a recipe. Also, the same recipe (i.e., a setting of the one or more process parameters) is used to process the wafers in one wafer lot. One or more individual process parameters of a particular recipe can be adjusted while processing the wafers in one wafer lot. The one or more process parameters can also be set to different values to define different recipes. Different recipes can be used to process different wafer lots. Thus, one recipe can be used to process one wafer lot, and another recipe can be used to process another wafer lot.

Fabrication tool 104 can be various types of fabrication tools, such as a coater/developer tool, plasma etch tool, cleaning tool, chemical vapor deposition (CVD) tool, and the like, that perform various fabrication processes. For example, when fabrication tool 104 is a coater/developer tool, the fabrication process includes depositing/developing a photoresist layer on one or more wafers 102. The one or more process parameters can include temperature. Thus, in this example, variations in temperatures used to perform the deposition/development process can result in a variation in the photoresist layer, such as the thickness of the photoresist layer, deposited/developed using the coater/developer tool.

As depicted in FIG. 1, after one or more semiconductor fabrication processes are performed on one or more wafers 102 in fabrication tool 104, one or more wafers 102 can be examined using optical metrology tool 106. As will be described in more detail below, optical metrology tool 106 can be used to determine one or more profile parameters of a structure formed on one or more wafers 102.

Figure 2:
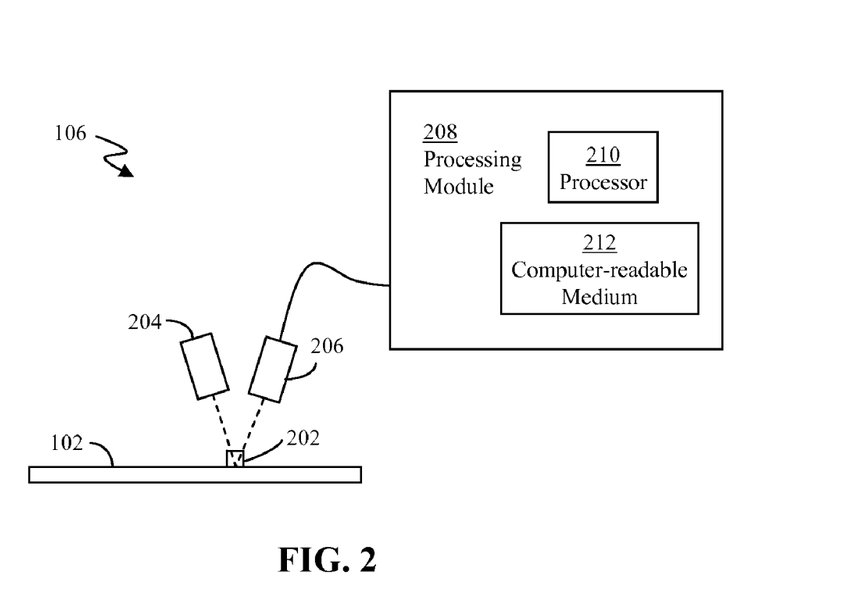
FIG. 2 depicts the exemplary optical metrology tool in more detail.

As depicted in FIG. 2, optical metrology tool 106 can include a photometric device with a source 204 and a detector 206. The photometric device can be a reflectometer, ellipsometer, hybrid reflectometer/ellipsometer, and the like.

A structure 202 formed on wafer 102 is illuminated by an incident beam from source 204. Diffracted beams are received by detector 206. Detector 206 converts the diffracted beam into a measured diffraction signal, which can include reflectance, tan ($\Psi$), cos ($\Delta$), Fourier coefficients, and the like. Although a zero-order diffraction signal is depicted in FIG. 2, it should be recognized that non-zero orders can also be used.

Optical metrology tool 106 also includes a processing module 208 configured to receive the measured diffraction signal and analyze the measured diffraction signal. Processing module 208 can include a processor 210 and a computer-readable medium 212. It should be recognized, however, that processing module 208 can include any number of components in various configurations.

In one exemplary embodiment, processing module 208 is configured to determine one or more profile parameters of structure 202 using any number of methods which provide a best matching diffraction signal to the measured diffraction signal. These methods can include a library-based process, or a regression based process using simulated diffraction signals obtained by rigorous coupled wave analysis and machine learning systems. See, U.S. Pat. No. 6,943,900, titled GENERATION OF A LIBRARY OF PERIODIC GRATING DIFFRACTION SIGNALS, filed on Jul. 16, 2001, issued Sep. 13, 2005, which is incorporated herein by reference in its entirety; U.S. Pat. No. 6,785,638, titled METHOD AND SYSTEM OF DYNAMIC LEARNING THROUGH A REGRESSION-BASED LIBRARY GENERATION PROCESS, filed on Aug. 6, 2001, issued Aug. 31, 2004, which is incorporated herein by reference in its entirety; U.S. Pat. No. 6,891,626, titled CACHING OF INTRA-LAYER CALCULATIONS FOR RAPID RIGROUS COUPLED-WAVE ANALYSES, filed on Jan. 25, 2001, issued May 10, 2005, which is incorporated herein by reference in its entirety; and U.S. patent application Ser. No. 10/608,300, Now Abandoned, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 3:
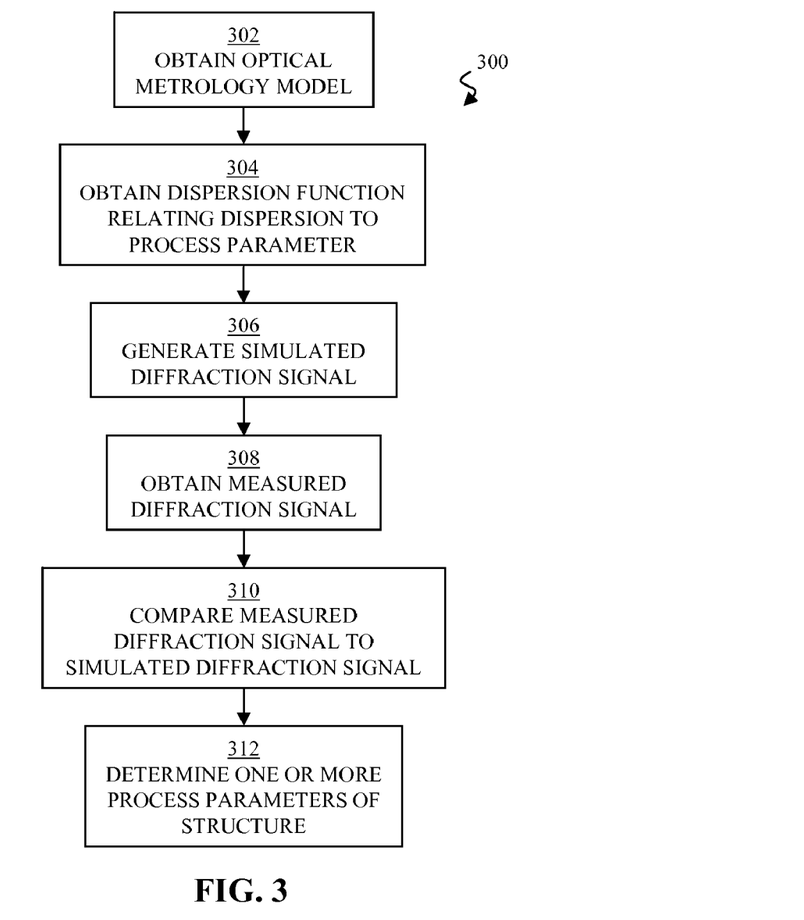
FIG. 3 is a flowchart of an exemplary process of examining a structure formed on a semiconductor wafer.

With reference to FIG. 3, an exemplary process 300 is depicted of examining a structure formed on a semiconductor wafer using an optical metrology model. It should be recognized that exemplary process 300 can be performed prior or subsequent to the structure actually being formed on the semiconductor wafer.

In step 302, an optical metrology model is obtained. The optical metrology model has one or more profile parameters, one or more process parameters, and a dispersion. A dispersion function is defined to relate the process parameter to the dispersion. The dispersion function can be expressed in various forms, such as wavelength by wavelength tablet form, the optical property of each wavelength can be a function of process parameters, or using dispersion models with model parameters varied with the process parameters. It should be recognized, however, that the optical metrology model can also include any number of additional parameters.

Figure 4:
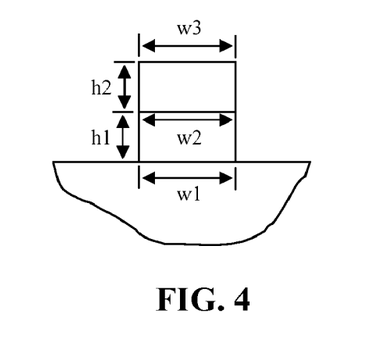
FIG. 4 depicts an exemplary structure characterized using a set of profile parameters.

The profile parameters of an optical metrology model characterize the geometric characteristics of a structure. For example, FIG. 4 depicts an exemplary structure characterized using a set of profile parameters. In particular, the bottom width of the first layer of the structure is characterized using profile parameter w1. The top width of the first layer and the bottom width of the second width of the structure are characterized using profile parameter w2. The top width of the second layer of the structure is characterized using profile parameter w3. The height of the first layer of the structure is characterized using profile parameter h1. The height of the second layer of the structure is characterized using profile parameter h2. It should be recognized that the structure can have various shapes and can be characterized using any number of profile parameters.

As described above, the process parameters of an optical metrology model characterize one or more process conditions of a process for fabricating a structure. For example, with reference to FIG. 1, the process parameter can characterize a process condition in fabrication tool 104 used to fabricate a structure on wafer 102. Examples of process parameters include deposition conditions (such as temperature, gas pressure, vaporization speed, etc.), annealing conditions, etching conditions (surface property change, etching residual components, etc.), and the like.

The dispersion characterizes optical properties of a material of the structure, the structure being formed by the process. For example, the dispersion can include the refractive indices (n) and the extinction coefficients (k) of a material. The optical metrology model can include separate dispersions for each material of the structure. For example, with reference again to FIG. 4, a first dispersion ($n_s$ & $k_s$) can correspond to the material of the substrate on which the structure is formed, such as silicon. A second dispersion ($n_1$ & $k_1$) can correspond to the material of the first layer of the structure, such as oxide. A third dispersion ($n_2$ & $k_2$) can correspond to the material of the second layer of the structure, such as poly-silicon.

With reference again to FIG. 3, in step 304, a dispersion function is obtained that relates the dispersion to at least one of the process parameters. For example, with reference to FIG. 4, the dispersion function can relate the dispersion corresponding to the material of the second layer of the structure ($n_2$ & $k_2$) to the temperature used in fabricating the structure in fabrication tool 104 (FIG. 1). An exemplary process of developing the dispersion function will be described in more detail below.

With reference again to FIG. 3, in step 306, a simulated diffraction signal is generated using the optical metrology model and a value for the at least one process parameter that is related to the dispersion by the dispersion function obtained in step 304 and a value for the dispersion. The value of the dispersion is calculated using the value for the at least one process parameter and the dispersion function. By relating the process parameter to the dispersion, the number of varying parameters in the optical metrology model is reduced with the desired accuracy, which increases the stability of the model.

For example, with reference again to FIG. 4, assume that the dispersion function obtained in step 304 (FIG. 3) related the dispersion corresponding to the material of the second layer of the structure ($n_2$ & $k_2$) to the temperature used in fabricating the structure in fabrication tool 104 (FIG. 1). Assume that in generating a simulated diffraction signal, a value for the temperature is specified (T1). Thus, the value of $n_2$ & $k_2$ is calculated using the dispersion function obtained in step 304 (FIG. 3) and T1.

As described in more detail below, the values of the remaining dispersions (ns & ks, n1 & k2) can be fixed to set values or floated, meaning that the values can be varied when additional simulated diffraction signals are generated. A set of values is specified for the profile parameters. The simulated diffraction signal is then generated using the values for the profile parameters, the process parameters, and the dispersions. In particular, the simulated diffraction signal can be generated by applying Maxwell's equations and using a numerical analysis technique to solve Maxwell's equations, such as Rigorous Coupled Wave Analysis (RCWA). See, U.S. patent application Ser. No. 09/770,997, Now U.S. Pat. No. 6,891,626, titled CACHING OF INTRA-LAYER CALCULATIONS FOR RAPID RIGOROUS COUPLED-WAVE ANALYSES, filed on Jan. 25, 2001, which is incorporated herein by reference in its entirety. The simulated diffraction signal can be generated using a machine learning system (MLS) employing a machine learning algorithm, such as back-propagation, radial basis function, support vector, kernel regression, and the like. See, U.S. patent application Ser. No. 10/608,300, Now Abandoned, titled OPTICAL METROLOGY OF STRUCTURES FORMED ON SEMI- CONDUCTOR WAFERS USING MACHINE LEARNING SYSTEMS, filed on Jun. 27, 2003, which is incorporated herein by reference in its entirety.

With reference again to FIG. 3, in step 308, a measured diffraction signal measured off the structure is obtained. For example, as described above, with reference to FIG. 1, after the structure is formed using fabrication tool 104, optical metrology tool 106 can be used to measure a diffraction signal off the structure formed on the wafer.

With reference again to FIG. 3, in step 310, the measured diffraction signal is compared to the simulated diffraction signal generated in step 306. In step 312, one or more profile parameters of the structure are determined based on the comparison of the measured diffraction signal to the simulated diffraction signal.

In particular, if the measured diffraction signal and the simulated diffraction signal match within one or more matching criteria such as goodness of fit and/or cost function, then the profile parameters used to generate the matching simulated diffraction signal are assumed to characterize the geometric shape of the structure. The dispersion used to generate the matching simulated diffraction signal is assumed to characterize the optical properties of the one or more materials of the structure to which the dispersion corresponds. The process parameters used to generate optical properties of the one or more materials and then generate the matching simulated diffraction signal are assumed to characterize the process conditions used to fabricate the structure.

If the measured diffraction signal and the simulated diffraction signal do not match within one or more matching criteria such as goodness of fit and/or cost function, then the measured diffraction signal is compared to one or more additional simulated diffraction signals until a match is found. The additional simulated diffraction signals are generated using a value of at least one profile parameter, process parameter, or dispersion that is different than the simulated diffraction signal that did not match the measured diffraction signal.

Values of one or more of the profile parameters (e.g., w1, w2, w3, h1, h2 of FIG. 4) can be changed in generating the additional simulated diffraction signals. Values of one or more of the process parameters can be changed in generating the additional simulated diffraction signals. If the values of the process parameters that are related to the dispersions in the dispersion function obtained in step 304 are changed, then the values of the dispersions are recalculated using the values of the process parameter and the dispersion function obtained in step 304. The values of the dispersions that are not related to process parameters in the dispersion function obtained in step 304 are fixed to set values or are allowed to float, meaning they are changed in generating the additional simulated diffraction signals.

For example, assume that the dispersion function obtained in step 304 related temperature to the dispersion corresponding to the material of the second layer of the structure ($n_2$ & $k_2$) depicted in FIG. 4. Assume that a first value of the temperature (T1) was used in generating the first simulated diffraction signal. As described above, a first value of $n_2$ & $k_2$ was calculated using the dispersion function obtained in step 304 and the first value of T1. Assume now that a second value of the temperature (T2) is used in generating an additional simulated diffraction signal (i.e., a second simulated diffraction signal). Thus, in the present example, a second value of $n_2$ & $k_2$ is calculated using the dispersion function obtained in step 304 and T2.

As described above, the remaining dispersions, which are not related to process parameters, can be fixed to set values or floated. For example, values of $n_s$ & $k_s$, which correspond to the material of the substrate on which the structure in FIG. 4 is formed, can be fixed to set values in generating the additional simulated diffraction signals. Values of $n_1$ & $k_1$, which corresponds to the material of the first layer of the structure in FIG. 4, can be floated (varied) in generating the additional simulated diffraction signals independent of the changes to the values for the process parameters.

In a library-based process, the additional simulated diffractions signals are generated in advance and stored in a library. In a regression-based process, the additional simulated diffraction signal is not generated until after the measured diffraction signal is found not to match the simulated diffraction signal to which it was compared.

Figure 5A:
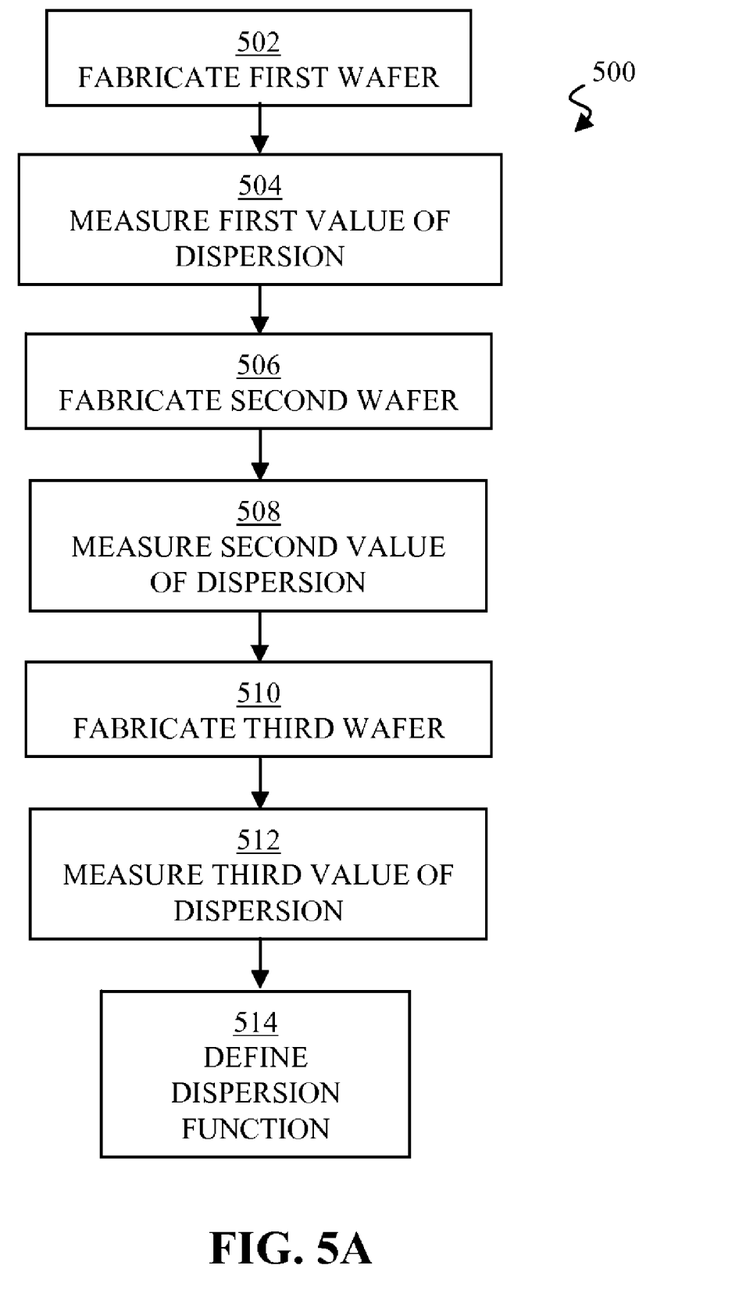
FIG. 5A is a flowchart of an exemplary process of defining a dispersion function relating a process parameter to a dispersion.

With reference to FIG. 5A, an exemplary process 500 is depicted of developing the dispersion function relating a process parameter to a dispersion. It should be recognized that exemplary process 500 can be performed in advance of exemplary process 300 (FIG. 3). It should also be recognized that exemplary process 500 can be performed in advance or subsequent to forming the structure to be examined.

In step 502, a first wafer is fabricated using a first value of the process parameter to be correlated to a dispersion. For example, assume the process parameter is temperature. Also assume that the dispersion is $n_2$ & $k_2$, which corresponds to the second layer of the structure depicted in FIG. 4. Thus, with reference to FIG. 1, the first wafer is fabricated using a first value of temperature in fabrication tool 104. In particular, the second layer of the structure depicted in FIG. 4 is formed using the first value of temperature in fabrication tool 104.

With reference again to FIG. 5A, in step 504, a first value of the dispersion is measured from the fabricated first wafer. Returning to the example above, the value of the n & k of the second layer of the structure depicted in FIG. 4 is measured.

In step 506, a second wafer is fabricated using a second value of the process parameter. In step 508, a second value of the dispersion is measured from the fabricated second wafer.

In step 510, a third wafer is fabricated using a third value of the process parameter. In step 512, a third value of the dispersion is measured from the fabricated third wafer.

The first, second, and third values for the process parameter used in steps 502, 506, and 510 are different from each other. In one exemplary embodiment, all other process parameters are kept constant in fabricating the first, second, and third wafers.

For example, assume again that the process parameter is temperature. Thus, in this example, with reference to FIG. 1, the first, second, and third wafers are fabricated in fabrication tool 104 using a first, second, and third temperature settings (T1, T2, and T3) that are different. All other process parameters, such as pressure, vaporization speed, and the like, are kept constant in fabricating the first, second, and third wafers in fabrication tool 104.

In one exemplary embodiment, the first, second, and third values of the dispersion can be measured using optical metrology tool 106. In particular, assume test structures with the shape shown in FIG. 4 are fabricated on the first, second, and third wafers using fabrication tool 104 (FIG. 1). Measured diffraction signals are measured off the test structures using optical metrology tool 106 (FIG. 1). The measured diffraction signals are compared to simulated diffraction signals to determine the first, second, and third values of the dispersions (e.g., n & k) of the second layers of the test structures on the first, second, and third wafers. Note, the simulated diffraction signals used in determining the first, second, and third values of n & k of the second layers of the test structures are generated by floating the values of n & k. It is understood that more than three sets of wafers can be fabricated with different values of the one or more process parameters in order to provide a bigger data sample for fitting the dispersion function.

In step 514, the dispersion function is defined using the first, second, and third values of the dispersion and the first, second, and third values of the process parameter. For example, a second-order polynomial can be fitted to the first, second, and third values of the dispersion and the first, second, and third values of the process parameter. In one exemplary embodiment, the dispersion function is defined for various wavelengths λ. Stated more generally, the second-order polynomial can be fitted to any number of dispersions (n & k) and process parameters (p) with coefficients: $an_0(\lambda)$, $an_1(\lambda)$, $an_2(\lambda)$, $ak_0(\lambda)$, $ak_1(\lambda)$, and $ak_2(\lambda)$ by minimizing the following error functions:

$$Enr(\lambda) = \sum_{j=1}^{k} (an_0(\lambda) + an_1(\lambda) \cdot p_j + an_2(\lambda) \cdot p_j^2 - n_j(\lambda))^2 \quad (1.1)$$

$$Ekr(\lambda) = \sum_{j=1}^{k} (ak_0(\lambda) + ak_1(\lambda) \cdot p_j + ak_2(\lambda) \cdot p_j^2 - k_j(\lambda))^2 \quad (1.2)$$

This fitting can be performed wavelength by wavelength. The number of samples (test structures) is larger than the number of the polynomial order plus one. It should be recognized that various functions can be fitted, such as a Taylor series in multi-dimensions.

Although a linear relationship of the variables is used in the examples above, it should be recognized that non-linear functional relationships between the variables can be used, such as arbitrary functions, composite functions, and the like. Least squares fit solutions to a polynomial may include the determinant, matrix, independent parameter solutions, and the like. Least squares fit to an arbitrary function may include nonlinear fitting methods, searching parameter space methods, grid search methods, gradient search methods, expansion methods, the Marquardt method, and the like. For a more detailed discussion of these techniques, see Bevington, et al., "Data Reduction and Error Analysis for the Physical Sciences," Third Edition, pages 116-177, which is incorporated herein by reference.

As described above, in step 306, a simulated diffraction signal using the optical metrology model is generated with the value of the dispersion being calculated using the value for the process parameter and the dispersion function. Continuing with the foregoing example, the value of n & k can be calculated for process parameter (p) at a wavelength as follows:

$$n(\lambda) = an_0(\lambda) + an_1(\lambda) \cdot p + an_2(\lambda) \cdot p^2 \quad (2.1)$$

$$k(\lambda) = ak_0(\lambda) + ak_1(\lambda) \cdot p + ak_2(\lambda) \cdot p^2 \quad (2.2)$$

The simulated diffraction signal is best matched with a measured diffraction signal. The profile parameters and process parameters that are used to generate the simulated diffraction signal that best matches the measured diffraction signal are assumed to characterize one or more profile parameters of the structure from which the measured diffraction signal was measured and the process parameters used to fabricate the structure.

The profile parameters and process parameters can be used to evaluate the fabrication tool and/or fabrication process used to fabricate the structure. For example, the profile parameters can be used to evaluate the fabrication tool used in the fabrication process. The process parameters can be used to monitor the process condition of the fabrication process performed using the fabrication tool. Thus, fabrication tool and/or fabrication process can be controlled to achieve a more stable performance and increase yield.

Figure 5B:
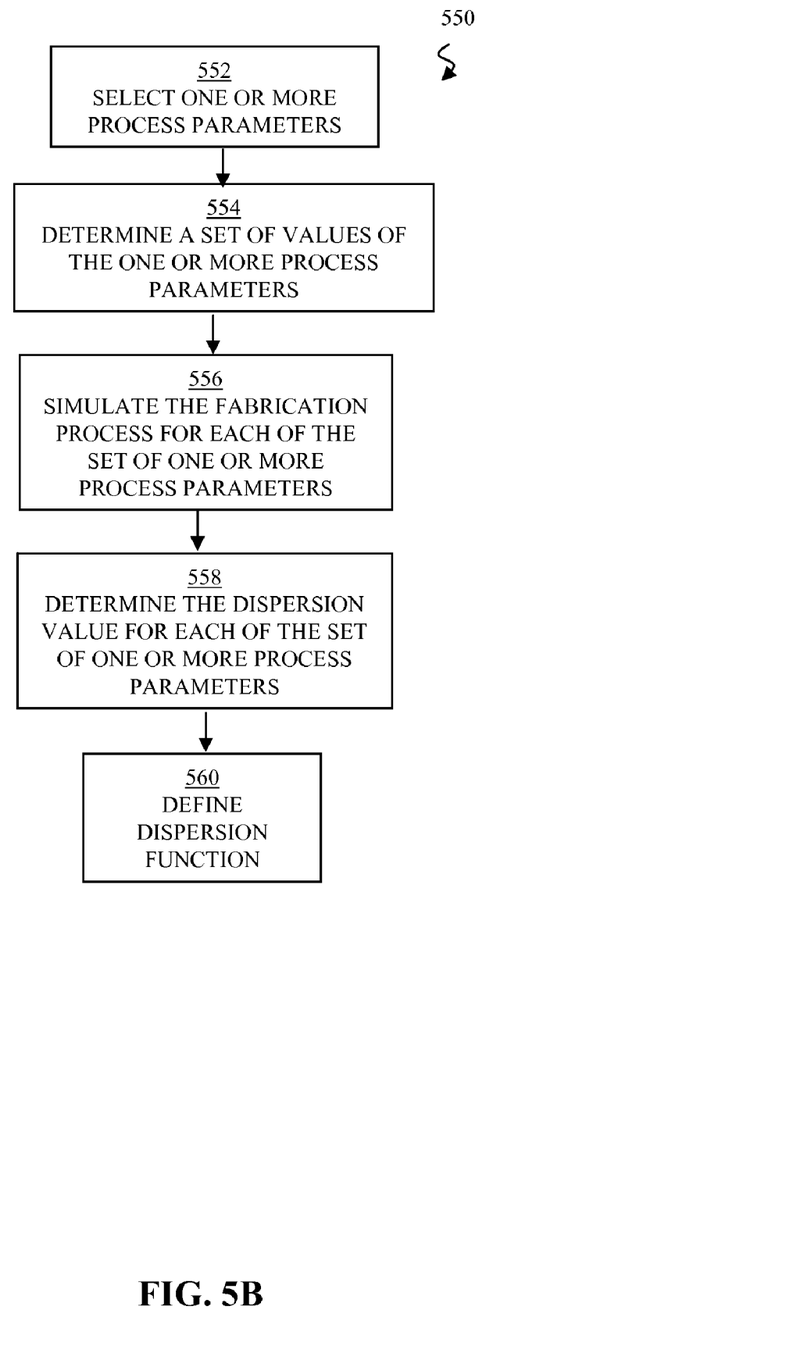
FIG. 5B is a flowchart of an exemplary process of defining a dispersion function relating a process parameter to a dispersion using a process simulator.

With reference to FIG. 5B, an exemplary process 550 is depicted of developing the dispersion function relating one or more process parameters to a dispersion using process simulation. As mentioned above, it should be recognized that exemplary process 550 can be performed in advance of exemplary process 300 (FIG. 3). In step 552, one or more process parameters of the fabrication process are selected. As mentioned above, the one or more process parameters can include deposition conditions, annealing conditions, etching conditions, temperature, gas pressure, vaporization speed, and the like. The etching conditions can include surface property changes, etching residual components, and the like. If the fabrication process is a deposition, the temperature of the chamber and/or the gas pressure may be selected as the process parameters. In step 554, a set of values of the one or more process parameters is determined based on empirical data or experience with the application or recipe. The one or more process parameters selected are the process parameter that will be correlated to the dispersion.

In step 556, fabrication of the wafer structure is simulated using a process simulator for each set of values of the selected one or more process parameters determined in step 554. Simulation of a fabrication process is typically done with process simulators such as Athena™ from Silvaco International, Prolith™ from KLA-Tencor, Solid-C from Sigma-C Gmbh, TCAD™ from Synopsis, and the like. Specifics of the recipe and the wafer structure and process parameters are provided to the process simulator. One of the typical output of the process simulation is the structure profile after the simulated process is completed. For example, assume the process parameter of interest is temperature. Also assume that the dispersion is $n_2$ & $k_2$, which corresponds to the second layer of the structure depicted in FIG. 4. Thus, simulation of fabrication of the wafer structure is simulated using a value of temperature. In particular, simulation of formation of the second layer of the structure depicted in FIG. 4 is done using the first value of temperature utilized by the process simulator.

With reference again to FIG. 5B, in step 558, a value of the dispersion is determined for the simulated wafer structure for each value of the one or more process parameters selected in step 552. Returning to the example above, the value of the n & k of the second layer of the structure depicted in FIG. 4 may be obtained by setting up n & k as an output of the process simulator or may be calculated using n & k simulation software. Examples of n & k simulation software include n & k Analyzer™ from n&k Technology, Prolith™ from KLA-Tencor, and the like. In one exemplary embodiment, all other process parameters are kept constant in the process simulation runs needed for step 558. For example, assume again that the process parameter is temperature. Thus, in this example, all other process parameters used in the process simulator, such as pressure, vaporization speed, and the like, are kept constant.

In step 560, the dispersion function is defined using the values of the dispersion and the values of the selected one or more process parameters. For example, if only one process parameter is selected, a second-order polynomial can be fitted to the values of the dispersion and the values of the process parameter. In one exemplary embodiment, the dispersion function is defined for various wavelengths λ. As described above, the second-order polynomial can be fitted to any number of dispersions (n & k) and process parameters (p) with coefficients: $an_0(\lambda)$, $an_1(\lambda)$, $an_2(\lambda)$, $ak_0(\lambda)$, $ak_1(\lambda)$, and $ak_2(\lambda)$ by minimizing the following error functions expressed in equation (1.1) and (1.2) above. This fitting can be performed wavelength by wavelength. The number of samples (test structures) is larger than the number of the polynomial order plus one. It should be recognized that various functions can be fitted, such as a Taylor series in multi-dimensions.

As mentioned above, a linear relationship of the variables is used in the examples above, it should be recognized that non-linear functional relationships between the variables can be used, such as arbitrary functions, composite functions, and the like. Least squares fit solutions to a polynomial may include the determinant, matrix, independent parameter solutions, and the like. Least squares fit to an arbitrary function may include nonlinear fitting methods, searching parameter space methods, grid search methods, gradient search methods, expansion methods, the Marquardt method, and the like. For a more detailed discussion of these techniques, see Bevington, et al., "Data Reduction and Error Analysis for the Physical Sciences," Third Edition, pages 116-177, which is incorporated herein by reference.

As described above, in step 306 of FIG. 3, a simulated diffraction signal using the optical metrology model is generated with the value of the dispersion being calculated using the value for the one or more process parameters and the dispersion function. Continuing with the foregoing example, the value of n & k can be calculated for process parameter (p) at a wavelength as depicted in equations (2.1) and (2.2). The simulated diffraction signal is best matched with a measured diffraction signal. The profile parameters and the one or more process parameters that are used to generate the simulated diffraction signal that best matches the measured diffraction signal are assumed to characterize one or more profile parameters of the structure from which the measured diffraction signal was measured and the one or more process parameters used to fabricate the structure. As also mentioned above, the profile parameters and one or more process parameters can be used to evaluate the fabrication tool and/or fabrication process used to fabricate the structure.

Figure 6:
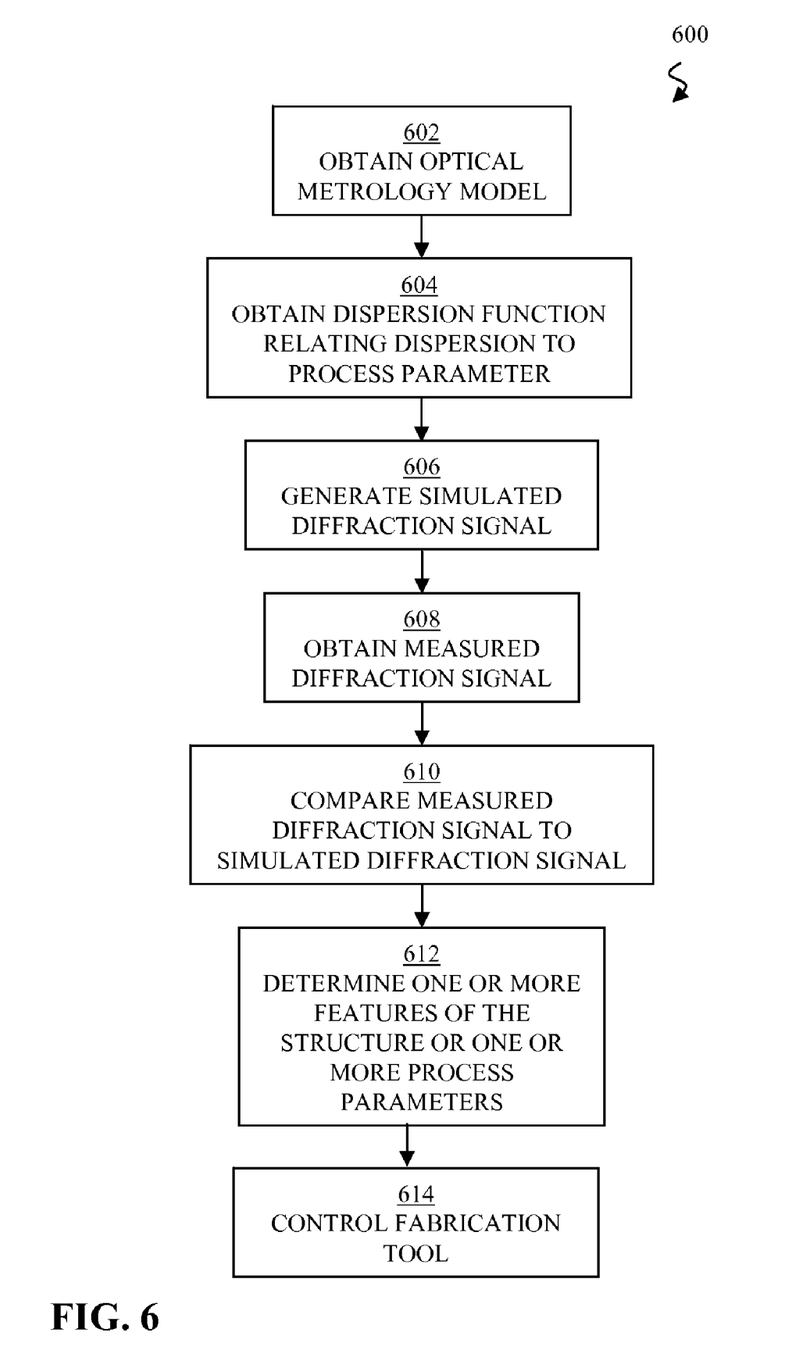
FIG. 6 is a flowchart of an exemplary process of controlling the fabrication tool.

With reference to FIG. 6, an exemplary process 600 is depicted for determining one or more profile parameters and/or one or more process parameters for automated process control. In step 602, an optical metrology model is created for a structure formed on a semiconductor wafer. The optical metrology model comprises one or more profile parameters, which characterize one or more geometric characteristics of the structure, one or more process parameters, which characterize one or more process conditions for fabricating the structure, and a dispersion, which characterizes optical properties of a material of the structure.

In step 604, a dispersion function is obtained that relates the dispersion to at least one of the one or more process parameters. In step 606, a simulated diffraction signal is generated using the optical metrology model and a value for the at least one of the process parameters and a value for the dispersion. The value for the dispersion is calculated using the value for the at least one of the process parameter and the dispersion function.

In step 608, a measured diffraction signal of the structure is obtained using an optical metrology tool. In step 610, the measured diffraction signal is compared to the simulated diffraction signal. In step 612, one or more profile parameters of the structure and one or more process parameters are determined based on the comparison in step 610. In step 614, the fabrication tool is controlled based on the determined one or more profile parameters of the structure.

Figure 7:
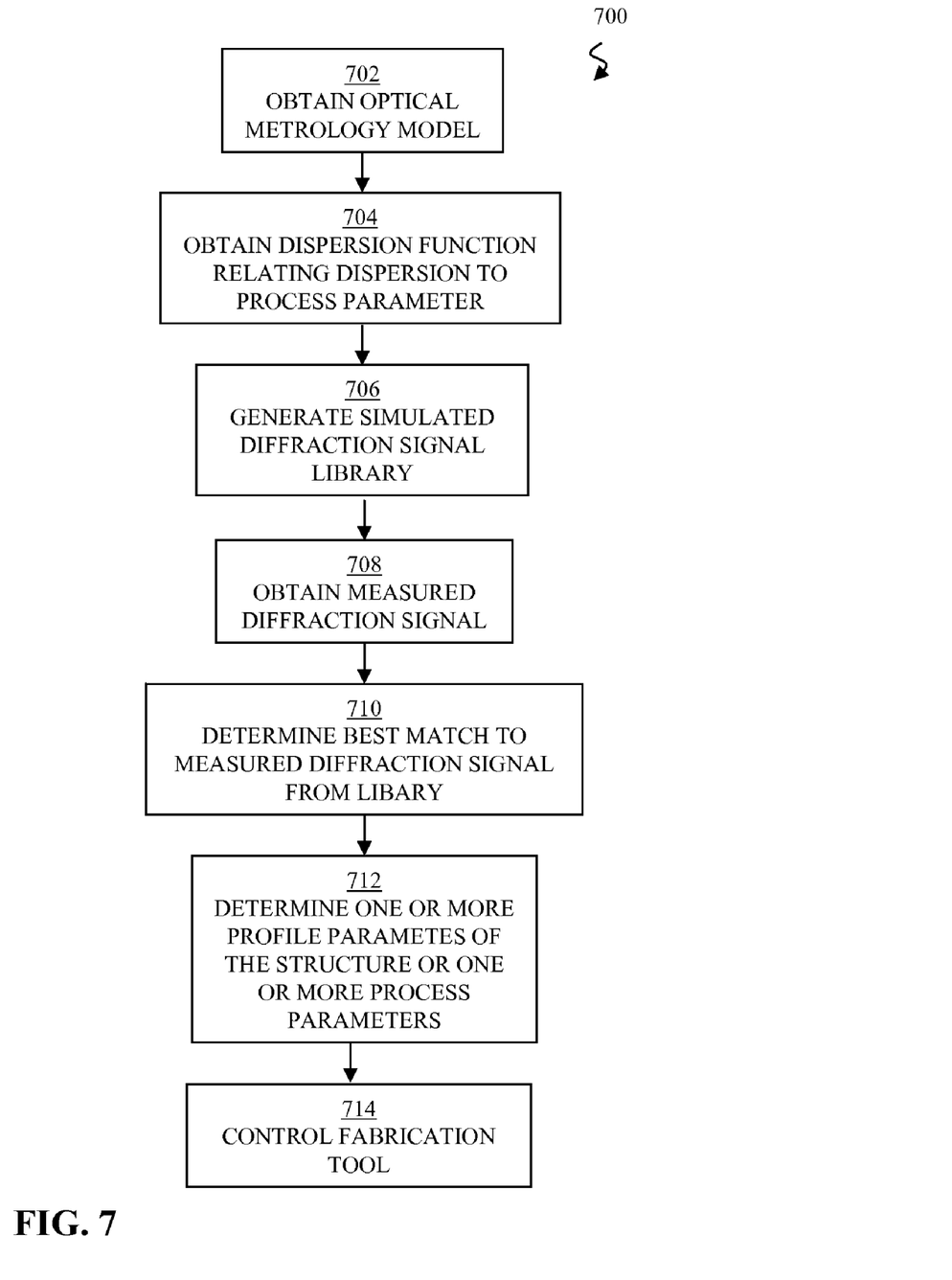
FIG. 7 is an exemplary flowchart for automated process control using a library.

With reference to FIG. 7, an exemplary process 700 is depicted for determining one or more profile parameters and one or more process parameters for automated process control using a library. In step 702, an optical metrology model is created for a structure formed on a semiconductor wafer. The optical metrology model comprises one or more profile parameters, which characterize one or more geometric characteristics of the structure, one or more process parameters, which characterize one or more process conditions for fabricating the structure, and a dispersion, which characterizes optical properties of a material of the structure.

In step 704, a dispersion function is obtained that relates the dispersion to at least one of the one or more process parameters. In step 706, a simulated diffraction signal library is generated using the optical metrology model and a value for the at least one of the process parameters and a value for the dispersion. The value for the dispersion is calculated using the value for at least one process parameter and the dispersion function.

In step 708, a measured diffraction signal of the structure is obtained using an optical metrology tool. In step 710, a best match to the measured diffraction signal is obtained from the library. In step 712, one or more profile parameters of the structure and one or more process parameters are determined based on the comparison in step 710. In step 714, the fabrication tool is controlled based on the determined one or more profile parameters of the structure or the determined one or more process parameters.

Figure 8:
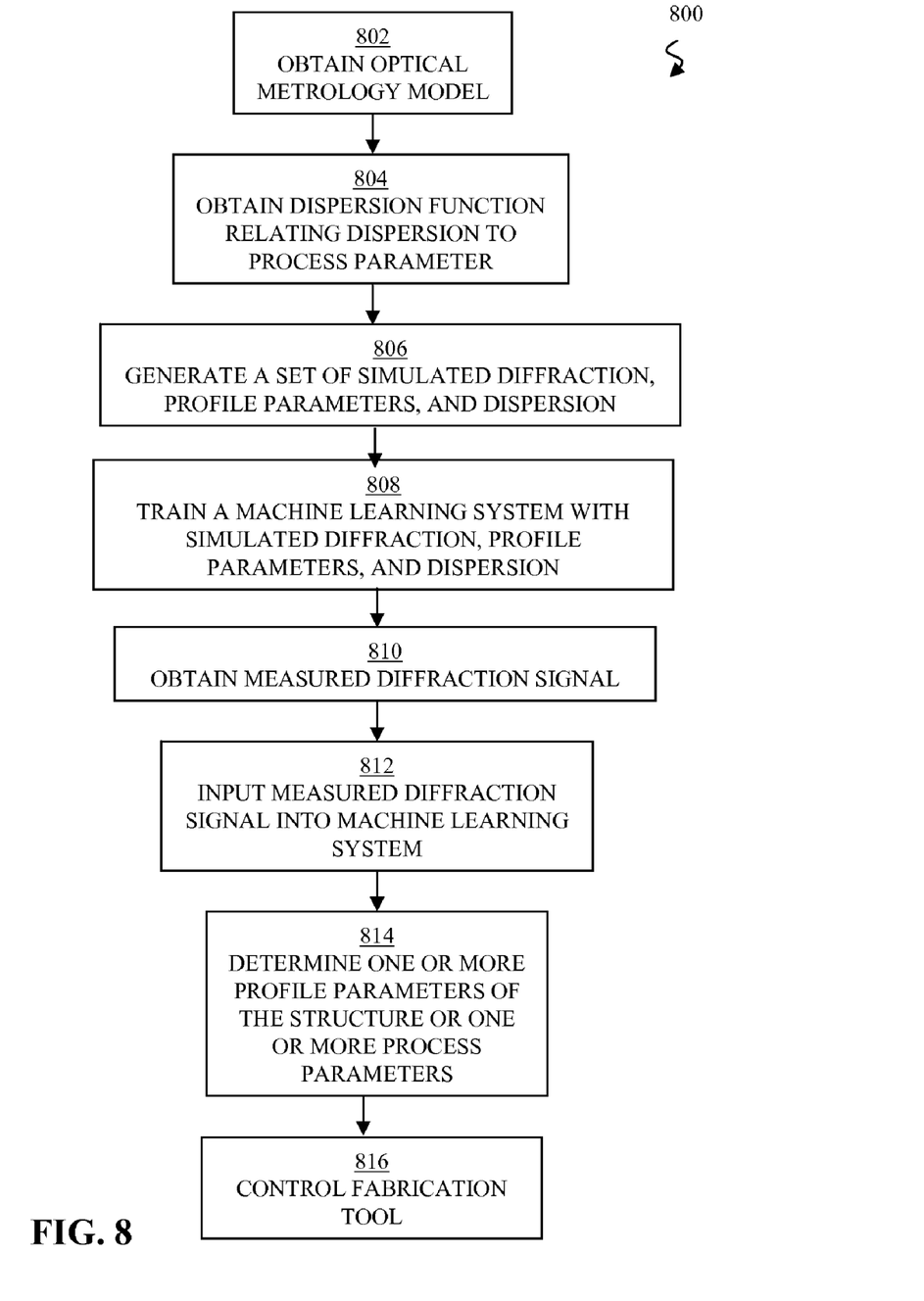
FIG. 8 is an exemplary flowchart for automated process control using a trained machine learning system.

With reference to FIG. 8, an exemplary process 800 is depicted for determining one or more profile parameters and one or more process parameters for automated process control using a trained machine learning system. In step 802, an optical metrology model is created for a structure formed on a semiconductor wafer. The optical metrology model comprises one or more profile parameters, which characterize one or more geometric characteristics of the structure, one or more process parameters, which characterize one or more process conditions for fabricating the structure, and a dispersion, which characterizes optical properties of a material of the structure.

In step 804, a dispersion function is obtained that relates the dispersion to at least one of the one or more process parameters. In step 806, a set of simulated diffraction signals is generated using the optical metrology model and a set of values for the at least one of the process parameters and a set of values for the dispersion. The value for the dispersion is calculated using the value for the at least one of the process parameter and the dispersion function.

In step 808, a machine learning system is trained to process the set of simulated diffraction signals as input and generate the value of the one or more profile parameters and one or more process parameters as output. In step 810, a measured diffraction signal of the structure is obtained using an optical metrology tool. In step 812, the measured diffraction signal is input into the trained machine learning system. In step 814, one or more profile parameters of the structure and one or more process parameters are determined based on the output of the machine learning system. In step 816, the fabrication tool is controlled based on the determined one or more profile parameters of the structure or the determined one or more process parameters.

The determined one or more process parameters can include deposition conditions, annealing conditions, or etching conditions, and the one or more fabrication processes can include a deposition process, annealing process, or etching process, respectively. The deposition conditions can include temperature, gas pressure, and vaporization speed. The etching conditions can include surface property changes, and etching residual components.

Figure 9:
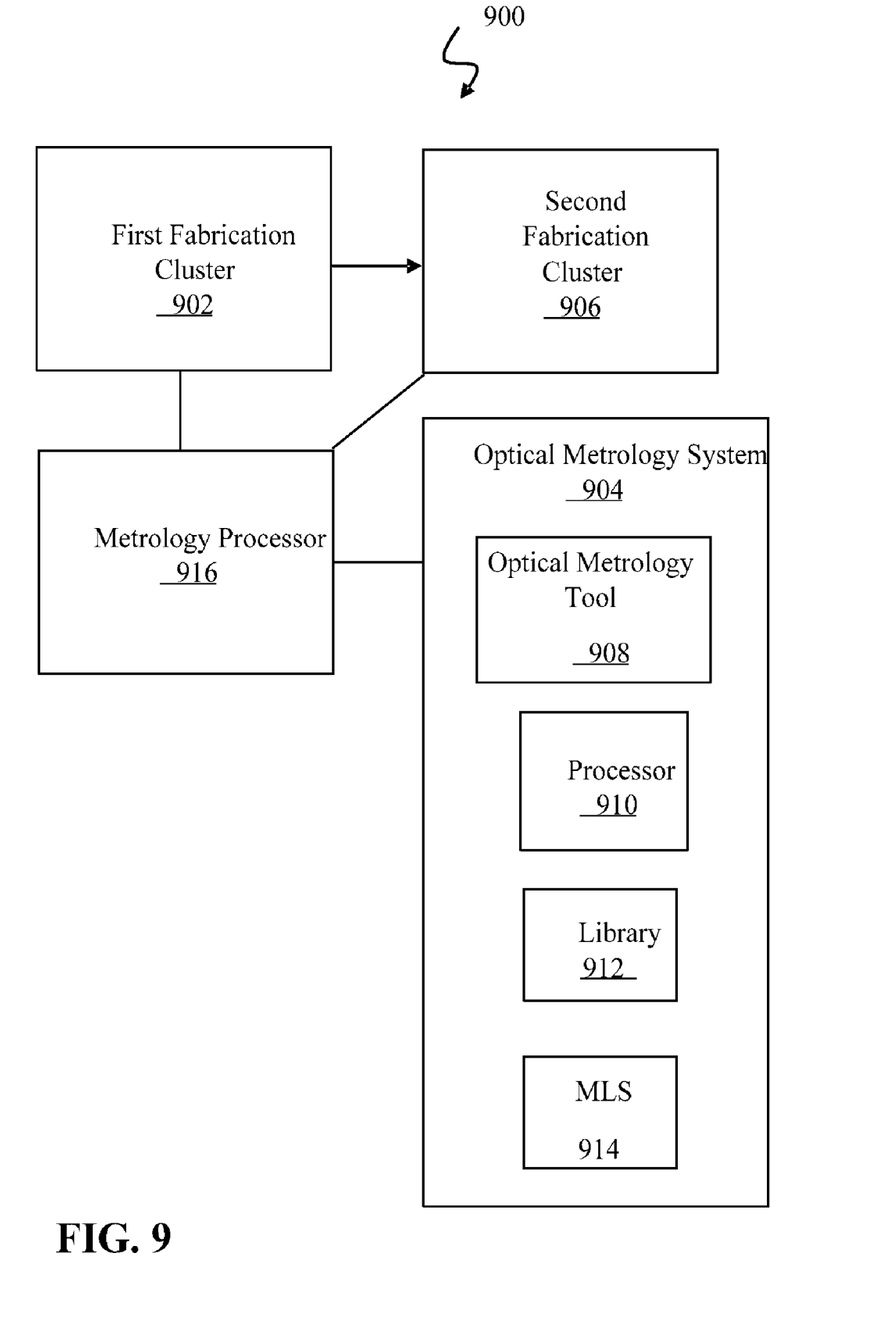
FIG. 9 is an exemplary block diagram of a system for determining and utilizing profile parameters and process parameters for automated process and equipment control.

FIG. 9 is an exemplary block diagram of a system for determining and utilizing profile parameters and process parameters for automated process and equipment control. System 900 includes a first fabrication cluster 902 and optical metrology system 904. System 900 also includes a second fabrication cluster 906. Although the second fabrication cluster 906 is depicted in FIG. 9 as being subsequent to first fabrication cluster 902, it should be recognized that second fabrication cluster 906 can be located prior to first fabrication cluster 902 in system 900 (e.g. and in the manufacturing process flow).

For example, a photolithographic process, such as exposing and/or developing a photoresist layer applied to a wafer, can be performed using the first fabrication cluster 902. In one exemplary embodiment, optical metrology system 904 includes an optical metrology tool 908 and processor 910. Optical metrology tool 908 is configured to measure a diffraction signal off the structure. Processor 910 is configured to compare the measured diffraction signal against the simulated diffraction signal. If the measured diffraction signal and the simulated diffraction signal match within a matching criterion, such as goodness of fit and/or cost function, one or more values of the profile parameters associated with the simulated diffraction signal are determined to be the one or more values of the profile parameters and the one or more process parameters associated with the measured diffraction signal are determined to be the one more values of the process parameters used to fabricate the structure.

In one exemplary embodiment, optical metrology system 904 can also include a library 912 with a plurality of simulated diffraction signals and corresponding one or more profile parameters and one or more process parameters. As described above, the library can be generated in advance; metrology processor 910 can compare a measured diffraction signal off the structure to the plurality of simulated diffraction signals in the library. When a matching simulated diffraction signal is found, the one or more values of the profile parameters and process parameters associated with the matching simulated diffraction signal in the library is assumed to be the one or more values of the profile parameters and process parameters used in the wafer application to fabricate the structure.

System 900 also includes a metrology processor 916. In one exemplary embodiment, processor 910 can transmit the one or more values of the one or more profile parameters and/or process parameters to metrology processor 916. Metrology processor 916 can then adjust one or more process parameters or equipment settings of first fabrication cluster 902 based on the one or more values of the one or more profile parameters and/or process parameters determined using optical metrology system 904. Metrology processor 916 can also adjust one or more process parameters or equipment settings of the second fabrication cluster 906 based on the one or more values of the one or more profile parameters and/or process parameters determined using optical metrology system 904. As noted above, fabrication cluster 906 can process the wafer before or after fabrication cluster 902. In another exemplary embodiment, processor 910 is configured to train machine learning system 914 using the set of measured diffraction signals as inputs to machine learning system 914 and profile parameters and process parameters as the expected outputs of machine learning system 914.

Furthermore, a computer readable medium (not shown) such as computer memory, disk, and/or storage may be used to store the instructions and computer programs to generate a simulated diffraction signal using a dispersion function relating process parameter to dispersion or to determine one or more profile parameters of a structure and one or more process parameters using an optical metrology model and generated simulated diffraction signals using the aforementioned method. In another embodiment, computer-executable instructions may be stored in a computer readable medium to determine one or more profile parameters and process parameters using a library comprising simulated diffraction signals and corresponding profile parameters and process parameters, and a measured diffraction signal. In another embodiment, computer-executable instructions may be stored in a computer readable medium to train a machine learning system to use a measured diffraction signal as input and generate one or more profile parameters and process parameters as output. In yet another embodiment, similar computer-executable instructions may be stored in a computer readable medium to control a photolithography cluster or other fabrication cluster using determined one or more profile parameters and process parameters to control a fabrication cluster.

Although exemplary embodiments have been described, various modifications can be made without departing from the spirit and/or scope of the present invention. Therefore, the present invention should not be construed as being limited to the specific forms shown in the drawings and described above.

We claim:

1. A method of relating one or more process parameters of a process to dispersion for use in optical metrology of a structure formed on a semiconductor wafer, the dispersion characterizing optical properties of one or more materials of the structure, the structure having a profile, the profile having profile parameters, the method comprising:

fabricating a first wafer using a first set of values for one or more process parameters specifying a process condition of the process in fabricating the structure;

measuring a first value of a dispersion from the fabricated first wafer;

fabricating a second wafer using a second set of values for the one or more process parameters;

measuring a second value of the dispersion from the fabricated second wafer;

fabricating a third wafer using a third set of values for the one or more process parameters, wherein the first, second, and third set of values for the one or more process parameters are different from each other;

measuring a third value of the dispersion from the fabricated third wafer;

defining a dispersion function to relate the one or more process parameters to the dispersion using the first, second, and third set of values for the one or more process parameter and the measured first, second, and third values of the dispersion;

generating a simulated diffraction signal, which characterizes the behavior of light diffracted from the structure, using a value of the one or more process parameters, the defined dispersion function, and profile parameters; and storing the simulated diffraction signal;

wherein the one or more process parameters are process conditions of the process, the process being a single step of semiconductor fabrication.

2. The method of claim 1, wherein all other process parameters are held constant in fabricating the first, second, and third wafers.

3. The method of claim 1, wherein the dispersion function is a linear relationship of the variables or a non-linear functional relationship between the variables, wherein non-linear functional relationships include arbitrary functions or composite functions.

4. The method of claim 1, wherein the dispersion includes a refractive index (n) parameter and an extinction coefficient (k) parameter.

5. The method of claim 1, wherein the one or more process parameters can include deposition conditions, annealing conditions, or etching conditions.

6. The method of claim 5, wherein the deposition conditions may include temperature, gas pressure or vaporization speed and wherein the etching conditions may include surface property changes or etching residual components.

7. A method of generating a simulated diffraction signal used in optical metrology of a structure formed on a semiconductor wafer, the method configured to use a minimum number of parameters in the simulated diffraction signal generation, the method comprising:
  generating a plurality of values for one or more process parameters, the one or more process parameters specifying process conditions in fabricating the structure, wherein each value of the one or more process parameters is different from the other values;
  fabricating a wafer structure using each of the plurality of values for the one or more process parameters;
  measuring a value of dispersion from each of the plurality of the fabricated wafer structures, the dispersion characterizing optical properties of a material of the structure;
  defining a dispersion function to relate the one or more process parameters to the dispersion using the generated values of the one or more process parameters and the measured values of the dispersion;
  generating a simulated diffraction signal, which characterizes the behavior of light diffracted from the structure, using the defined dispersion function; and
  storing the simulated diffraction signal and the corresponding one or more process parameters;
  wherein the one or more process parameters are process conditions of the process, the process being a single step of semiconductor fabrication.

8. A method of generating a simulated diffraction signal used in optical metrology of a structure formed on a semiconductor wafer, the method comprising:
  selecting one or more process parameters specifying a process condition in fabricating a structure;
  obtaining a set of values of the selected one or more process parameters;
  simulating fabrication of the structure using a process simulator and using values from the set of values of the selected one or more process parameters, the fabrication simulation generating a profile of the structure, the profile of the structure having profile parameters;
  determining a dispersion value for each simulation of fabrication of the structure using the generated profile of the structure;
  defining a dispersion function to relate the one or more process parameters to the dispersion using the obtained set values of the selected one or more process parameters and the determined dispersion values;
  generating a simulated diffraction signal, which characterizes the behavior of light diffracted from the structure, using a value of the one or more process parameters, the defined dispersion function, and profile parameters; and
  storing the simulated diffraction signal;
  wherein the one or more process parameters are process conditions of the process, the process being a single step of semiconductor fabrication.

9. The method of claim 8 wherein all other process parameters except the selected one or more process parameters are held constant during simulation of the structure fabrication.

10. The method of claim 8 wherein the dispersion function is a linear relationship of the variables or a non-linear functional relationship between the variables, wherein linear functional relationships may include polynomial functions and non-linear functional relationships may include arbitrary functions or composite functions.

11. A system to relate one or more process parameters of a process to dispersion for use in optical metrology of a structure formed on a semiconductor wafer, the dispersion characterizing optical properties of one or more materials of the structure, the structure having a profile, the profile having profile parameters, the system comprising:
  a fabrication tool configured to fabricate a first wafer using a first value for a process parameter specifying a process condition, a second wafer using a second value for the process parameter, and a third wafer using a third value for the process parameter, wherein the first, second, and third values for the process parameter are different from each other; and
  an optical metrology tool configured to measure a first value of a dispersion, which characterizes optical properties of a material of the structure, from the fabricated first wafer, a second value of the dispersion from the fabricated second wafer, a third value of the dispersion from the fabricated third wafer, wherein a dispersion function is defined to relate the process parameter to the dispersion using the first, second, and third values for the process parameter and the measured first, second, and third values of the dispersion, and wherein the simulated diffraction signal, which characterizes the behavior of light diffracted from the structure, is generated using a value of the one or more process parameters, the defined dispersion function, and profile parameters;
  wherein the one or more process parameters are process conditions of the process, the process being of semiconductor fabrication.

12. The system of claim 11, wherein the dispersion includes a refractive index (n) parameter and an extinction coefficient (k) parameter.

13. The system of claim 11, wherein the one or more process parameters may include deposition conditions, annealing conditions, or etching conditions;
  wherein the deposition conditions may include temperature, gas pressure or vaporization speed and the etching conditions may include surface property changes or etching residual components.

14. A system to generate a simulated diffraction signal used in optical metrology of a structure, the structure having profile parameters, the system comprising:
  a process simulator configured to simulate a process to fabricate a structure using a set of values for one or more process parameters specifying a process condition;
  a dispersion analyzer configured to generate a value of a dispersion, which characterizes optical properties of a material of the structure; and
  a processor configured to define dispersion function to relate the one or more process parameters to the dispersion using the set of values for the one or more process parameters and corresponding generated values of the dispersion configured to generate a simulated diffraction signal, the simulated diffraction signal characterizing behavior of light diffracted off the structure and using a value of the one or more process parameters, the defined dispersion function, and profile parameters, and configured to use a minimum number of parameters in the simulated diffraction signal generation;

wherein the one or more process parameters are process conditions of the process, the process being a single step of semiconductor fabrication.

* * * * *